(12) United States Patent
Lin et al.

(10) Patent No.: US 8,134,021 B2
(45) Date of Patent: Mar. 13, 2012

(54) PHOSPHORUS-CONTAINING BISPHENOLS AND PREPARING METHOD THEREOF

(75) Inventors: Ching-Hsuan Lin, Taichung (TW); Chia-Wei Chang, Hsinchu (TW); Tsung-Li Lin, Yunlin County (TW); Kuen-Yuan Hwang, Hsinchu County (TW); An-Pang Tu, Hsinchu County (TW); Fang-Hsien Su, Hsinchu County (TW)

(73) Assignees: National Chunghsing University, Taichung (TW); Chang Chun Plastics Co., Ltd, Taipei (TW)

( * ) Notice: Subject to any disclaimer, the term of this patent is extended or adjusted under 35 U.S.C. 154(b) by 244 days.

(21) Appl. No.: 12/502,241

(22) Filed: Jul. 14, 2009

(65) Prior Publication Data
US 2010/0016585 A1    Jan. 21, 2010

(30) Foreign Application Priority Data
Jul. 15, 2008   (TW) ............................... 97126836 A (51) Int. Cl.
*C07D 413/10*   (2006.01)
*C07F 9/28*   (2006.01)
(52) U.S. Cl. ........................................... 558/82; 568/14
(58) Field of Classification Search ............... 558/82; 568/14
See application file for complete search history.

(56) References Cited

OTHER PUBLICATIONS

Cai et al. Journal of Polymer Chemistry, Part A: Polymer Chemistry (2005), 43(13), 2862-2873.*

Lin et al. Journal of Polymer Chemistry, Part A: Polymer Chemistry (2008), 46(23), 7898-7912.*

* cited by examiner

*Primary Examiner* — Kahsay T Habte
(74) *Attorney, Agent, or Firm* — CKC & Partners Co., Ltd.

(57) ABSTRACT

The Phosphorus-containing bisphenols and preparing method thereof are disclosed. A method for producing the phosphorus-containing bisphenol of the formula (1) includes reacting compounds respectively defined by a formula (a), (b), (c) and an acid catalyst to yield compounds of phosphorus-containing bisphenol.

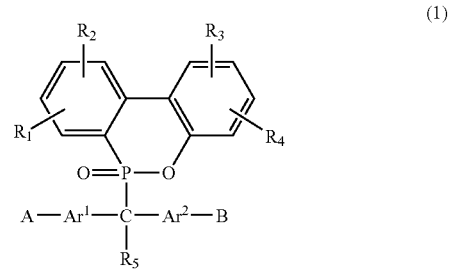

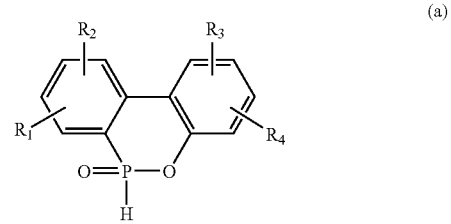

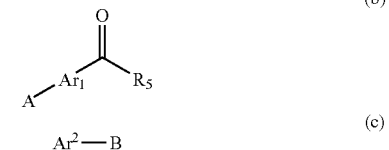

15 Claims, 6 Drawing Sheets

PHOSPHORUS-CONTAINING BISPHENOLS AND PREPARING METHOD THEREOF

RELATED APPLICATIONS

The application claims priority to Taiwan Application Serial Number 97126836, filed Jul. 15, 2008, which is herein incorporated by reference.

BACKGROUND

1. Field of Invention

The disclosure relates to phosphorus-containing bisphenols. More particularly, the disclosure relates to phosphorus-containing bisphenols with reactive functional groups and the methods of preparing thereof.

2. Description of Related Art

Since ancient times, fire accidents have always been a threat to human safety and cause economical damage. Various flame retardant materials are adapted to different applications; therefore the choice of the flame retardant materials should be based on the actual needs. Recently, the halogenated flame retardant compounds have been used as typical components of flame-retardant composites. However, the generations of corrosive and toxic substance (such as dioxin) from the halogenated flame retardants can cause metabolic disorder syndromes such as nervous, sleep disorders, headaches, eye disease, arteriosclerosis, liver tumors, and so on. Moreover, the relationship between the toxic substances and cancer has been reported in animal experiment.

In recent years, the organic phosphorus compounds that can provide good flame retardant properties for polymers have been investigated. In case of fire situation, the organic phosphorus-based polymers will not produce toxic gases. Furthermore, the organic phosphorus-based polymers provide advantages in processability, less usage amount and less release of smoke as compared to the halogenated flame-retardants. Particularly, an organic phosphorus-based polymer with reactive functional groups in the main structure will exhibit more flame-retardant effect.

DOPO (9,10-dihydro-9-oxa-10-phosphaphenanthrene-10-oxide) is a phosphorus-containing compound with active atomic hydrogen that can react with electron-deficient compounds, such as benzoquinone, oxirane, maleic acid, bismaleimide, diaminobenzophenone, and terephthaldicarboxaldehyde. The derivatives of DOPO are already attracting greater attention from researchers of the academic and industrial field.

In the early 1990s, a compound DOPOBQ was synthesized by reacting DOPO with benzoquinone has a formula represented as follow:

DOPOBQ

DOPOBQ is used as a precursor of bisphenol monomer to form bisphenol-based resin. However, the industrial applications are limited by its poor solubility and reactivity and high cost of the starting materials of DOPO.

SUMMARY

The disclosure is directed to a series of phosphorus-containing bisphenols to expand the applications of phosphorus-containing compounds.

The disclosure is directed to a method for producing the phosphorus-containing bisphenol with reactive sites that allow for functionalization.

According to one embodiment of the disclosure, a phosphorus-containing compound has a formula represented by formula (1):

wherein $R_1$, $R_2$, $R_3$, and $R_4$ independently are hydrogen atom, halogen atom, an alkyl group having 1-10 carbon atoms, an oxyalkyl group having 1-10 carbon atoms, a haloalkyl group having 1-10 carbon atoms, a cyclic alkyl group having 3-10 carbon atoms, —$CF_3$, or —$OCF_3$; $R_5$ is n alkyl group having 1-10 carbon atoms, an oxyalkyl group having 1-10 carbon atoms, a haloalkyl group having 1-10 carbon atoms, a cyclic alkyl group having 3-10 carbon atoms, —$CF_3$, —$OCF_3$, halogen atom, or —$Ar^3$; A and B are independently selected form the group consisting of —OH, —$OCH_3$, —$OCH_2CH_3$, —OCN, and glycidyl ether having the structure as follows:

$$-O-\overset{H_2}{C}-\triangle$$

—$Ar^1$ and —$Ar^2$ of Formula (1), and —$Ar^3$ of $R_5$ are independently selected from the group consisting of following groups:

wherein $R_6$ is hydrogen atom, a halogen atom, an alkyl group having 1-10 carbon atoms, an oxyalkyl group having 1-10 carbon atoms), a haloalkyl group having 1-10 carbon atoms, a cyclic alkyl group having 3-10 carbon atoms, —$CF_3$, or —$OCF_3$, m is an integer from 0 to 4; $R_7$ is —OH, —$NH_2$, —$NO_2$, —SH, —COOH, —$SO_3H$, —COH, —$NHCOCH_3$ and —$OCH_3$, and z is an integer from 1 to 20; $R_8$ is nil or —$CH_2$—$(CH_3)_2CH_2$, —CO, —$SO_2$—, —O, —NH; and $R_9$ is nil or —$(CH_2)_p$, and p is an integer from 1 to 20.

According to one embodiment of the disclosure, a method for producing the phosphorus-containing bisphenol with reactive functional groups includes reacting compounds respectively defined by a formula (a), (b), (c) with an acid catalyst to synthesize the phosphorus-containing bisphenol according to formula (1) where $R_5$ is methyl group or phenyl group.

The yielded phosphorus-containing bisphenol with reactive functional groups is available for further synthesizing phosphorus-containing epoxy, phosphorus-containing cyanate resin, or phosphorus-containing benzoxazine.

According to one embodiment of the disclosure, a phosphorus-containing benzoxazine was prepared by following exemplary route:

wherein the R' is hydrogen atom, alkyl of 1-6 carbon atoms, oxyalkyl of 1-6 carbon atoms, phenyl group, biphenyl group, halogen, nitro group, phenoxy group, cyclic alkyl of 3-7 carbon atoms, or a group with following structure:

and $R_n$ is hydrogen atom, alkyl of 1-6 carbon atoms, oxyalkyl of 1-6 carbon atoms, phenyl group, biphenyl group, halogen, nitro group, phenoxy group, and cyclic alkyl of 3-7 carbon atoms, $R_m$ is —$NH_2$, —$NO_2$, —SH, —COOH, —$SO_3H$, —COH, —$NHCOCH_3$, or —$OCH_3$, and n, m independently are an integer from 0 to 4.

According to the above mentioned, the phosphorus-containing bisphenols with reactive functional groups of embodiments of the disclosure are available for further synthesizing phosphorus-containing derivates, such as epoxy resin, cyanate resin, benzoxazine resin, etc. In addition, the phosphorus-containing bisphenols can be employed as an epoxy resin hardener. Therefore, the phosphorus-containing bisphenols can be used to replace the DOPOBQ to provide a more economically flame retardant material for industrial applications. Since the reactive functional groups are introduced into the side chain of the phosphorus-containing bisphenol, their are not only allow for directly attaching the epoxy rings of epoxy resins but also provide improved heat resistance and mechanical properties than conventional phosphorus-containing resin.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiments, with reference made to the accompanying drawings as follows.

DETAILED DESCRIPTION

Reference will now be made in detail to the embodiments of the disclosure, examples of which are illustrated in the accompanying drawings.

In one aspect of the disclosure is directed to phosphorus-containing bisphenolic compounds with reactive functional groups and the derivatives thereof. According to embodiments of the disclosure, two phosphorus-containing bisphenolic compounds with reactive functional groups having a main structure presented in formula (1) are presented, and -A, —B, —Ar$^1$, and —Ar$^2$ are the reactive functional groups.

(1)

$R_1$, $R_2$, $R_3$, and Rd independently are hydrogen atom, halogen atom, an alkyl group having 1-10 carbon atoms, an oxyalkyl group having 1-10 carbon atoms, a haloalkyl group having 1-10 carbon atoms, a cyclic alkyl group having 3-10 carbon atoms, —CF$_3$, or —OCF$_3$; $R_5$ is an alkyl group having 1-10 carbon atoms, an oxyalkyl group having 1-10 carbon atoms, a haloalkyl group having 1-10 carbon atoms, a cyclic alkyl group having 3-10 carbon atoms, —CF$_3$, —OCF$_3$, halogen atom, or —Ar$^3$. -A and —B are independently selected form the group consisting of —OH, —OCH$_3$, —OCH$_2$CH$_3$, —OCN, and glycidyl ether having the structure as follows:

and —Ar$^1$ and —Ar$^2$ of formula (1), and —Ar$^3$ of R$_5$ are independently selected from the group consisting of following groups:

$R_8$ is hydrogen atom, halogen atom, an alkyl group having 1-10 carbon atoms, an oxyalkyl group having 1-10 carbon atoms, a haloalkyl group having 1-10 carbon atoms, a cyclic alkyl group having 3-10 carbon atoms, —CF$_3$, or —OCF$_3$; m is an integer from 0 to 4. $R_7$ is —OH, —NH$_2$, —NO$_2$, —SH, —COOH, —SO$_3$H, —COH, —NHCOCH$_3$ and —OCH$_3$, and z is an integer from 1 to 20. $R_8$ is nil or —CH$_2$—(CH$_3$)$_2$CH$_2$, —CO, —SO$_2$—, —O, —NH; and R$_9$ is nil or —(CH$_2$)$_p$, and p, z independently are an integer from 1 to 20.

In one embodiment, a phosphorus-containing bisphenolic compound according to formula (1) having a methyl group in R$_5$, two phenyl groups respectively in —Ar$^1$ and —Ar$^2$, and two hydroxyl groups respectively in -A and —B is presented as formula (2):

(2)

In another embodiment, a phosphorus-containing bisphenolic compound according to formula (1) having a phenyl group in R$_5$, two phenyl groups respectively in —Ar$^1$ and —Ar$^2$, and two hydroxyl groups respectively in -A and —B is presented as formula (6):

(6)

The phosphorus-containing bisphenolic compounds of formula (2) and formula (6) respectively having two reactive side-chain hydroxyl groups and two reactive benzene rings are available for further synthesizing phosphorus-containing derivates, such as epoxy resin, cyanate resin, benzoxazine resin, etc.

In another aspect of the disclosure is directed to the preparation of the phosphorus-containing bisphenolic compounds with reactive functional groups and the derivatives thereof.

A method for synthesizing the phosphorus-containing bisphenol of the formula (1) includes reacting compounds respectively defined by a formula (a), (b), (c), and an acid catalyst to yield compound of formula (1), the exemplary synthesizing route of the compound of formula (1) is illustrated below:

$R_1, R_2, R_3$, and $R_4$ independently are hydrogen atom, halogen atom, an alkyl group having 1-10 carbon atoms, an oxyalkyl group having 1-10 carbon atoms, a haloalkyl group having 1-10 carbon atoms, a cyclic alkyl group having 3-10 carbon atoms, $-CF_3$, or $-OCF_3$; $R_5$ is an alkyl group having 1-10 carbon atoms, an oxyalkyl group having 1-10 carbon atoms, a haloalkyl group having 1-10 carbon atoms, a cyclic alkyl group having 3-10 carbon atoms, $-CF_3$, $-OCF_3$, halogen atom, or $-Ar^3$. A and B are independently selected form the group consisting of $-OH$, $-OCH_3$, $-OCH_2CH_3$, $-OCN$, and glycidyl ether having the structure as follows:

and $-Ar^1$ and $-Ar^2$ of formula (1), and $-Ar^3$ of $R_5$ are independently selected from the group consisting of following groups:

$R_6$ is hydrogen atom, halogen atom, an alkyl group having 1-10 carbon atoms, an oxyalkyl group having 1-10 carbon atoms, a haloalkyl group having 1-10 carbon atoms, a cyclic alkyl group having 3-10 carbon atoms, $-CF_3$, or $-OCF_3$; m is an integer from 0 to 4. $R_7$ is $-OH$, $-NH_2$, $-NO_2$, $-SH$, $-COOH$, $-SO_3H$, $-COH$, $-NHCOCH_3$ and $-OCH_3$, and z is an integer from 1 to 20. $R_8$ is nil or $-CH_2-(CH_3)_2 CH_2$, $-CO$, $-SO_2-$, $-O$, $-NH$; and $R_9$ is nil or $-(CH_2)_p$, and p, z independently are an integer from 1 to 20.

For one embodiment of the disclosure, the compounds of formula (2) is prepared by reacting compounds respectively defined by formula (a), (b), (c) with an acid catalyst. The $R_1$, $R_2$, $R_3$, and $R_4$ of the compound of formula (a) independently are hydrogen atom; the $-Ar^1$, -A, and $R_5$ of the compound of formula (b) respectively is phenyl group, hydroxyl group and methyl group; and $Ar^2$ and B of the compound of formula (c) respectively are phenyl group and hydroxyl group.

For another embodiment of the disclosure, the compound of formula (6) is prepared by the same procedures above-mentioned with the exception that the $R_5$ of the compound of formula (b) is phenyl group.

The exemplary preparation of the compounds of formula (2), (6) and the derivates thereof are stated in the following embodiments.

Embodiment (A)

Preparation of Phosphorus-Containing Bisphenolic Compound of Formula

The phosphorus-containing bisphenolic compounds with reactive functional groups presented as formula (2) was prepared by reacting DOPO with phenol, 4'-Hydroxyacetophenone, and an acid catalyst. The synthesizing route of the compound of formula (2) is illustrated below:

(2)

The exemplary preparation process of the compound of formula (2) is icy stated in the following description:

10.81 g (0.05 mole) of DOPO, 22.28 g (0.25 mole) of phenol, 6.81 g (0.05 mole) of 4'-Hydroxyacetophenone, and 0.216 g (2 wt % which is based on weight of DOPO) of p-toluenesulfonic acid were added and stirred in a 250 ml 3-neck flask reactor at room temperature in advance. The reactants were is stirred constantly at 130° C. for 24 hours to form a mixture, and then the temperature of the reaction system is recooled down to room temperature. The treated mixture was dissolved in ethanol and added into hot water to precipitate crude product. The crude product was filtrated and dried in a vacuum oven to obtain a purified phosphorus-containing bisphenolic compound of formula (2) and the yield was 85%, the melting point of the compound was 360° C.

Figure 1A:
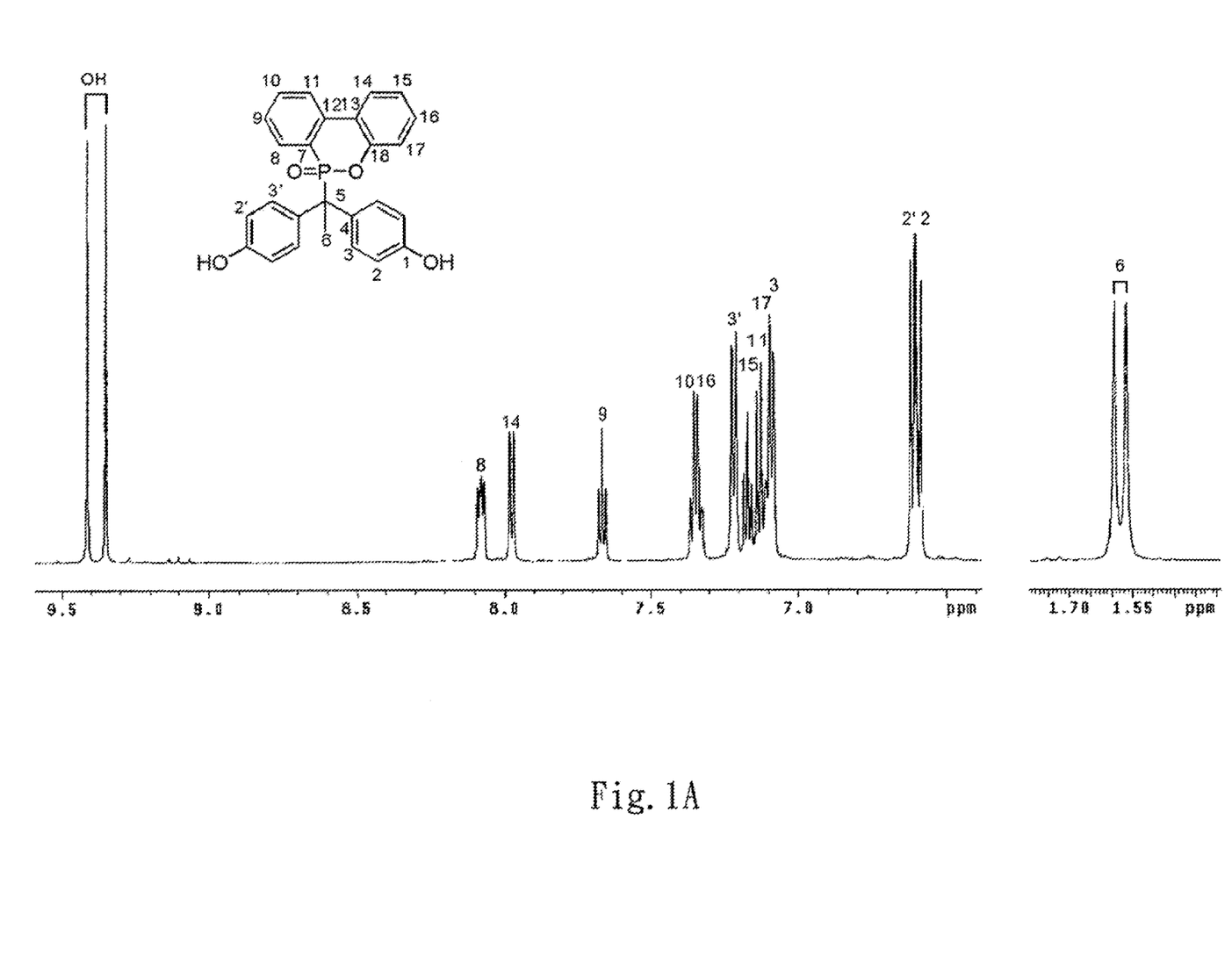
FIG. 1A is a diagram of $^1H$ NMR spectra of the phosphorus-containing bisphenolic compound of formula (2)
Figure 1B:
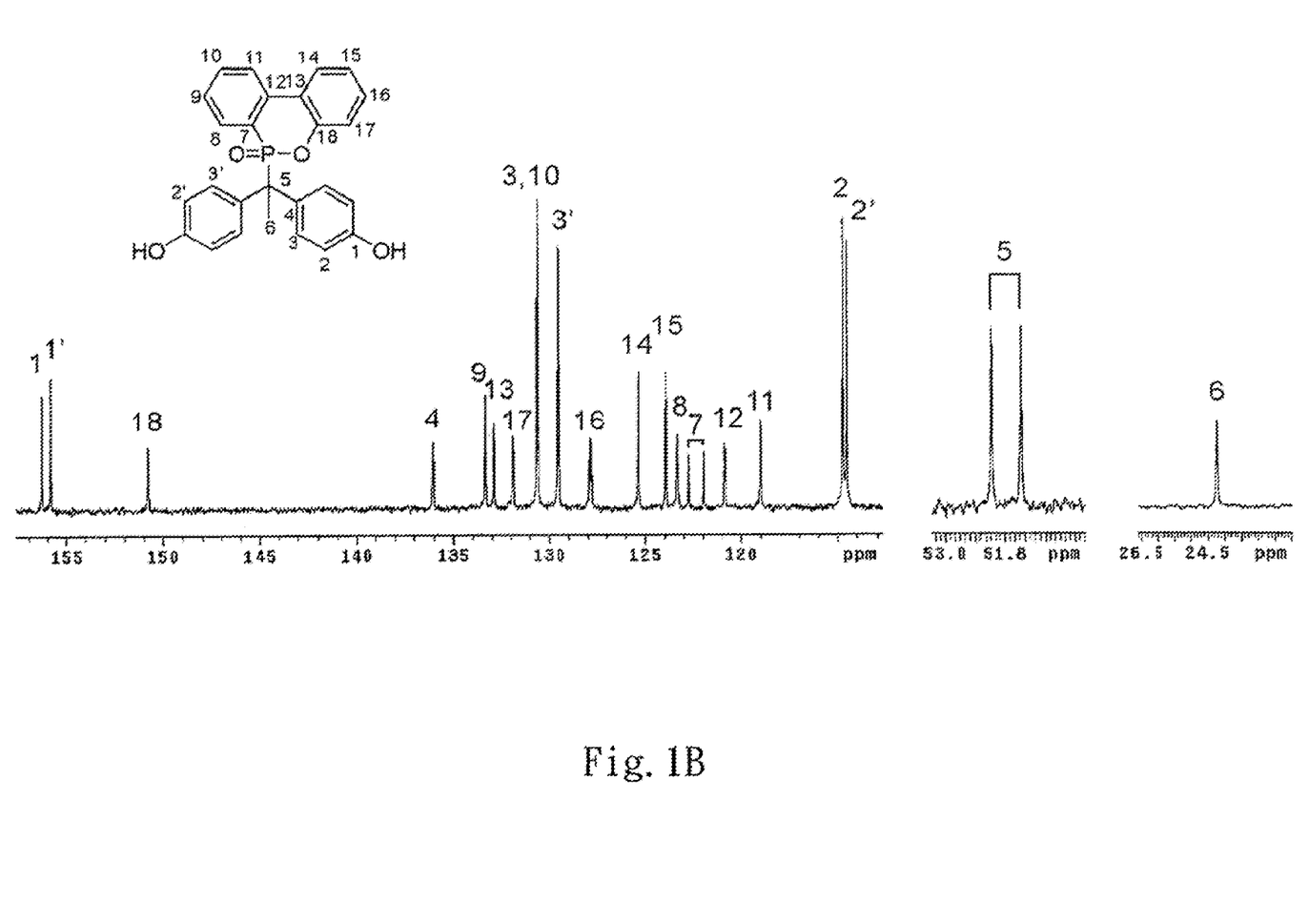
FIG. 1B is a diagram of $^{13}C$ NMR spectra of the phosphorus-containing bisphenolic compound of formula (2)
Figure 1C:
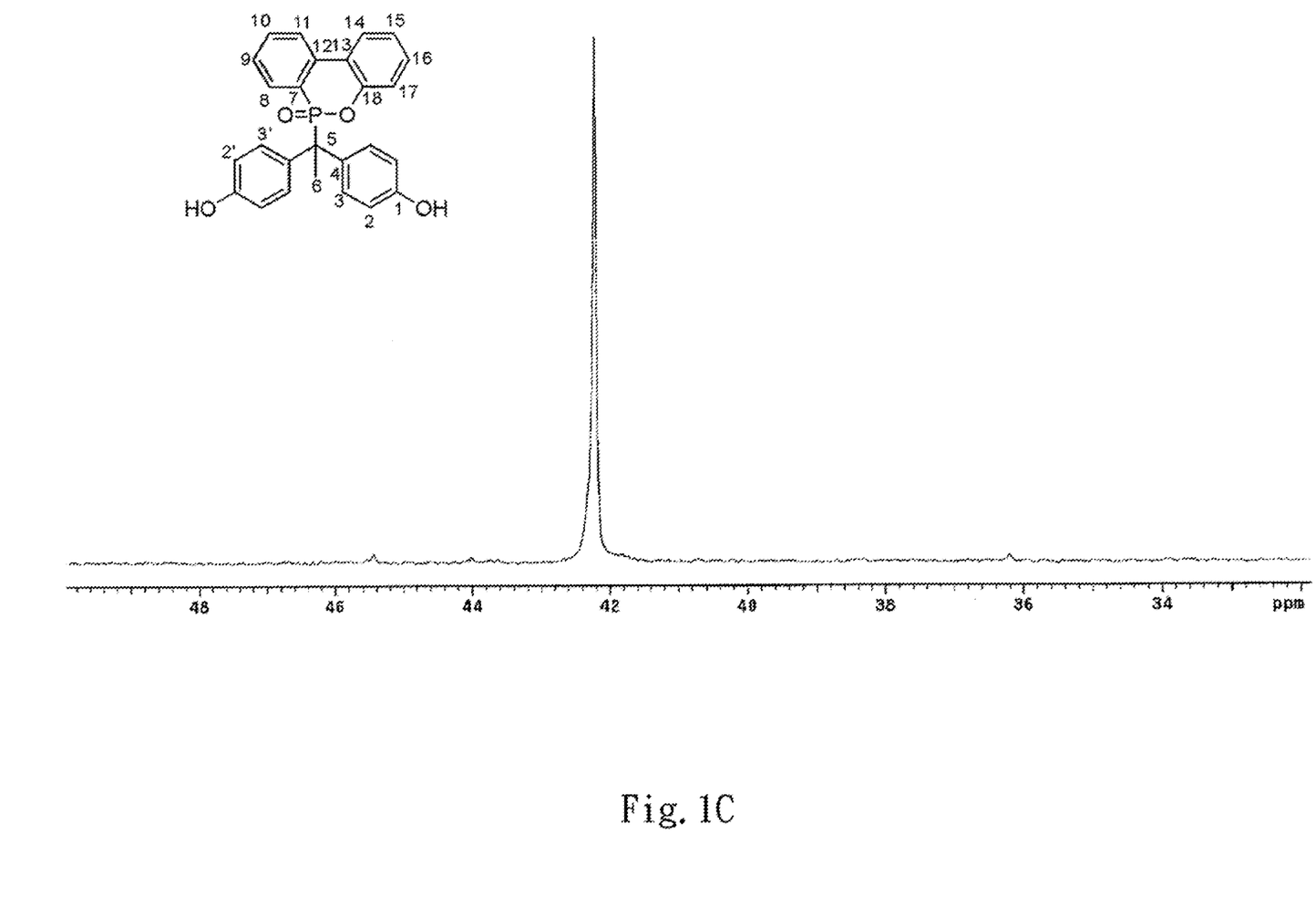
FIG. 1C is a diagram of $^{31}P$ NMR spectra of the phosphorus-containing bisphenolic compound of formula (2)

The chemical structure of the product was confirmed by $^1$H NMR, $^{13}$C NMR, and $^{31}$P NMR. FIGS. 1A-1C respectively are $^1$H NMR, $^{13}$C NMR, and $^{31}$P NMR spectrum of the product.

The exemplary derivates of the compound of formula (2) and the synthesizing routes of the derivates are respectively stated and illustrated in the to following examples:

Example 1

An Epoxy Resin Derived Form the Compound of Formula (2)

Two exemplary epoxy group-containing organic groups may be attached to the two functional groups (—OH) of the compound of formula (2) to form a is compound presented as formula (3):

(2)

(3)

The exemplary preparation process of the compound of formula (3), derived from the compound of formula (2), is stated in the following description:

214 g of compound of formula (2) and 925 g of epichlorohydrin were added into a 3-liter reactor and stirred to form a homogeneous solution under atmospheric pressure and then heated to 70° C. under absolute pressure of 190 mm Hg. 200 g of 20% aqueous sodium hydroxide solution was added into the homogeneous solution at a constant rate over 4 hours and the water contained in the reaction system was azeotropically distilled at the same time. After the reaction had completed, the remaining epichlorohydrin and solvent were removed by vacuum distillation. Sodium chloride contained in the resulting crude epoxy resin was dissolved in methyl ethyl ketone and deionized water and washed off with water. The solvent was distillated from the resulting crude epoxy resin under reduced pressure to yield a white epoxy resin with 242 equivalents of epoxy.

Example 2

A Cyanate Ester Derived Form the Compound of Formula (2)

In another example, the compound of formula (2) may derive a cyanate ester by substituting the hydrogen atom of the phenolic OH groups with cyanide groups. The derived cyanate ester is presented as formula (4)

The exemplary preparation process of the compound of formula (4), derived from the compound of formula (2), is stated in the following description:

A cool anhydrous acetone solution was prepared by mixing 70 g of anhydrous acetone and 7.2027 g (0.068 mole) of BrCN in a 3-neck flask reactor at −15° C. and then stirred at −25° C. constantly. A mixture was prepared by mixing 8.5684 g (0.02 mole) of the phosphorus-containing bisphenolic compound of formula (2) with 6.1321 g (0.0606 mole) of $Et_3N$ and dissolved in 100 g of acetone. The mixture was slowly poured into the 3-neck flask reactor through a funnel at −30° C. to proceed a reaction for 2 hours. Since the temperature of the reaction system was re-cooled to −30° C., the reacted mixture was dripped into deionized water to wash and remove the ammonium bromide.

After a filtration operation of the yield solution, some precipitates were obtained. The precipitates were extracted by solvent extraction ($CH_2Cl_2/H_2O$) and the organic phase was collected. After the organic phase was dried by magnesium sulfate anhydrous and the $CH_2Cl_2$ removed by rotary evaporator, the solid cyanate ester of formula (4) was obtained.

Example 3

A Benzoxazine Resin Derived Form the Compound of Formula (2)

In another example, the compound of formula (2) may derive a benzoxazine by fusing two oxazine rings with the active benzene rings of the compound of formula (2). The derived benzoxazine is presented as formula (5):

The exemplary preparation process of the compound of formula (5), derived from the compound of formula (2), is stated in the following description:

To prepare a 5 M solution A', 3.246 g (0.04 mole) of formaldehyde was dissolved in 1.2 ml of dioxane. A 10 M solution B' was prepared by dissolving 1.55 g (0.02 mole) of methylamine in 3 ml dioxane. Solution A' was loaded in a 100 ml reactor and nitrogen was introduced into the reactor in an ice bath. Solution B' was dripped into the reactor at a rate of 1 drop per second under 10° C. The reaction was further progressed for 30 min after the solution B had dropped out. 4.284 g (0.01 mole) of the phosphorus-containing bisphenolic compound of formula (2) was loaded into the reactor and the working temperature was increased until reflux. Then the reaction was further progressed for 10 hours and the solvents were removed by vacuum filtration. The product was dissolved in $CH_2Cl_2$ solution and extracted by 0.1 M NaOH extraction. The extract was washed by deionized water for several times. After the water contained in the reaction system was removed with magnesium sulfate anhydrous, the product was filtrated and dried in a vacuum oven to obtain a pink solid with 76% yield.

Embodiment (B)

Preparation of Phosphorus-Containing Bisphenolic Compound of Formula (6)

The phosphorus-containing bisphenolic compounds with reactive functional groups of formula (6) was prepared by reacting DOPO with phenol, 4'-Hydroxybenzophenone, and an acid catalyst. The synthesizing route of the compound of formula (6) is illustrated below:

The exemplary preparation process of the compound of formula (6) is stated in the following description:

10.81 g (0.05 mole) of DOPO, 22.28 g (0.25 mole) of phenol, 9.91 g (0.05 mole) of 4'-Hydroxybenzophenone, and 0.216 g (2 wt % which is based on weight of DOPO) of p-toluenesulfonic acid were added and stirred in a 250 ml 3-neck flask reactor at room temperature in advance. The reactants were stirred constantly at 130° C. for 24 hours to form a mixture and then recooled down to room temperature. The treated mixture was dissolved in ethanol and added into hot water to precipitate the product. The product was filtrated and dried in a vacuum oven to obtain a purified phosphorus-containing bisphenolic compound of formula (6) and the yield was 87%, the melting point was 288° C.

Figure 2A:
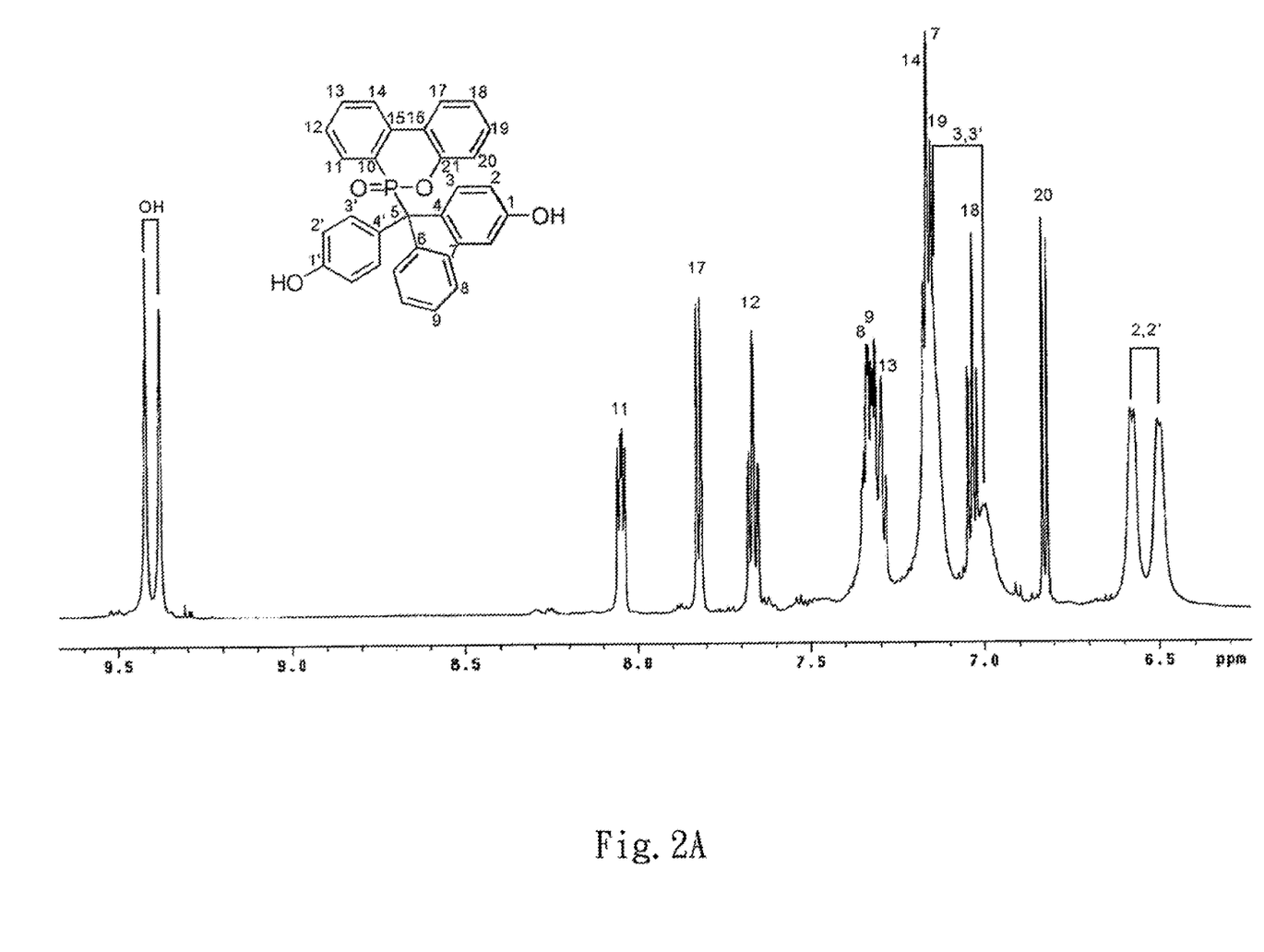
FIG. 2A is a diagram of $^1H$ NMR spectra of the phosphorus-containing bisphenolic compound of formula (6)
Figure 2B:
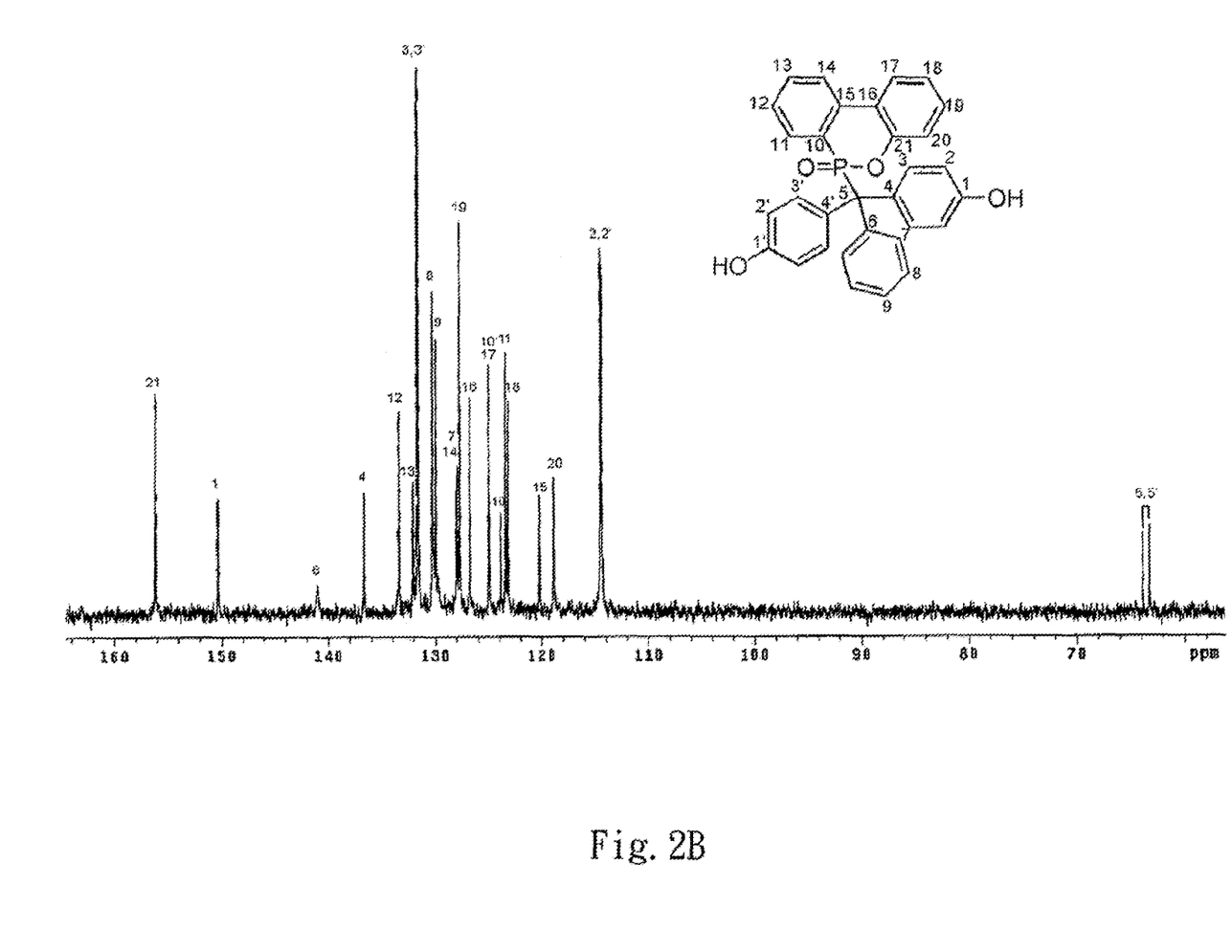
FIG. 2B is a diagram of $^{13}C$ NMR spectra of the phosphorus-containing bisphenolic compound of formula (6)
Figure 2C:
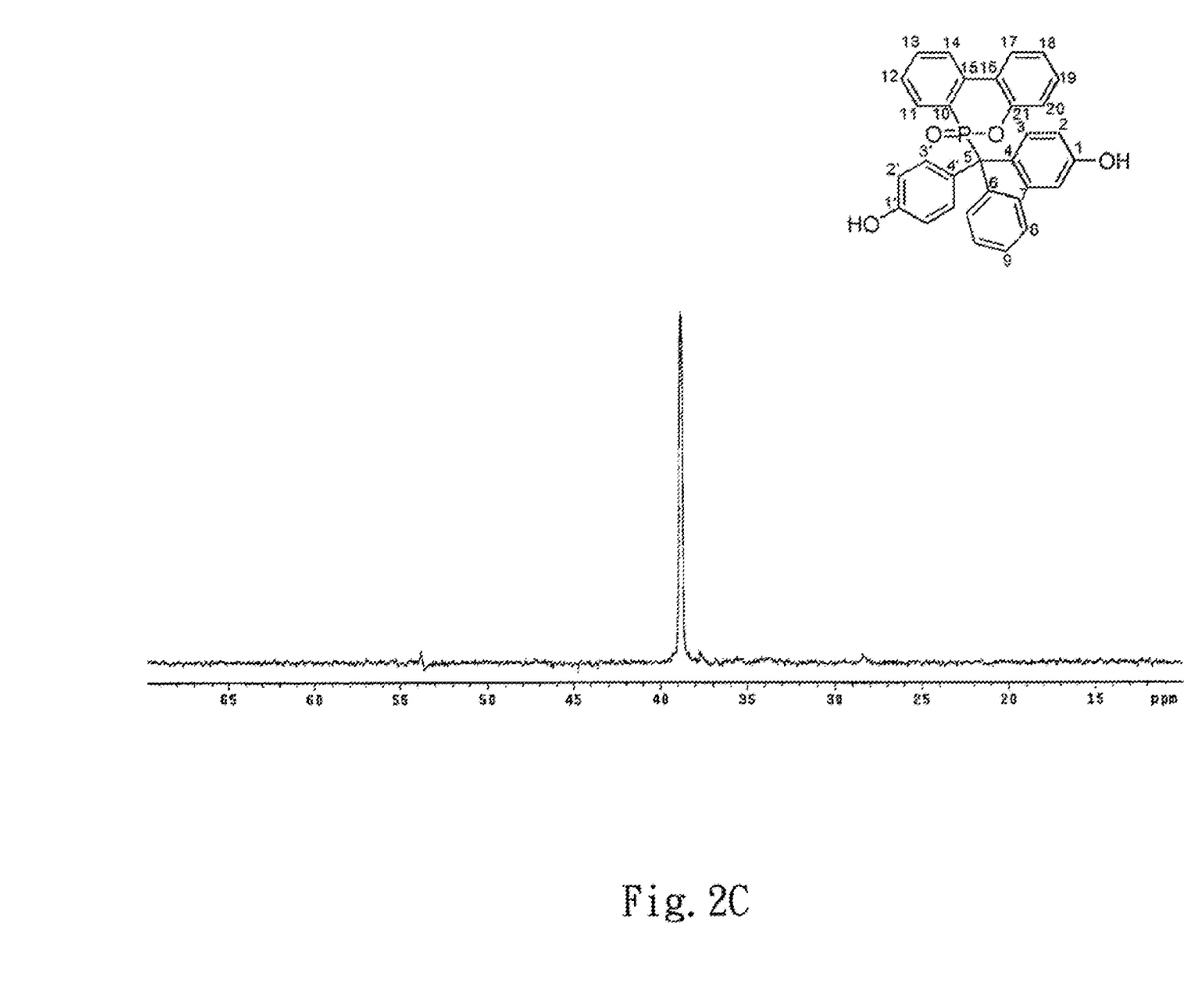
FIG. 2C is a diagram of $^{31}$P NMR spectra of the phosphorus-containing bisphenolic compound of formula (6).

The chemical structure of the product was confirmed by $^1$H NMR, $^{13}$C NMR, and $^{31}$P NMR. FIGS. 2A-2C respectively are $^1$H NMR, $^{13}$C NMR, and $^{31}$P NMR spectrum of the product.

The exemplary derivates of the compound of formula (6) and the synthesizing routes of the derivates are respectively stated and illustrated in the following examples:

Example 4

An Epoxy Resin Derived Form the Compound of Formula (6)

Two exemplary epoxy group-containing organic groups may be attached to the two functional groups (—OH) of the compound of formula (2) to form a compound presented as formula (6):

The exemplary preparation process of the compound of formula (7), derived from the compound of formula (6), is stated in the following description:

245 g of phosphorus-containing bisphenolic compound of formula (6) and 925 g of epichlorohydrin were added into a 3-liter reactor and stirred to form a homogeneous solution under atmospheric pressure and then heated to 70° C. under absolute pressure of 190 mm Hg. 200 g of 20% aqueous sodium hydroxide solution was added into the homogeneous solution at a constant rate over 4 hours and the water contained in the reaction system was azeotropically distilled at the same time. After the reaction had completed, the remaining epichlorohydrin and solvent were removed by vacuum distillation. Sodium chloride contained in the resulting crude epoxy resin was dissolved in methyl ethyl ketone and deionized water and washed off with water. The solvent was distillated from the resulting crude epoxy resin under reduced pressure to yield a white epoxy resin with 286 equivalents of epoxy.

Example 5

A Cyanate Ester Derived Form the Compound of Formula (6)

In another example, the compound of formula (6) may derive a cyanate ester by substituting the hydrogen atom of the phenolic OH groups with cyanide groups. The derived cyanate ester is presented as formula (8):

The exemplary preparation process of the compound of formula (8), derived from the compound of formula (6), is stated in the following description:

A cool anhydrous acetone solution was prepared by mixing 70 g of anhydrous acetone and 7.2027 g (0.068 mole) of BrCN in a 3-neck flask reactor at −15° C. and then stirred at −25'C constantly. A mixture was prepared by mixing 9.8096 g (0.02 mole) of the phosphorus-containing bisphenolic compound of formula (6) with 6.1321 g (0.0606 mole) of Et$_3$N and dissolved in 100 g of acetone anhydrous. The mixture was slowly poured into the 3-neck flask reactor through a funnel at −30° C. to proceed a reaction for 2 hours. Since the temperature of the reaction system was re-cooled to −30° C., the reacted mixture was dripped into deionized water to wash and remove the ammonium bromide. After the yield solution was filtrated, some precipitates were obtained. The precipitates were extracted by solvent extraction (CH$_2$Cl$_2$/H$_2$O) and the organic phase was collected. After the organic phase was dried by magnesium sulfate anhydrous and the CH$_2$Cl$_2$ removed by rotary evaporator, the solid cyanate ester of formula (8) was obtained.

Example 6

A Benzoxazine Resin Derived Form the Compound of Formula (6)

In another example, the compound of formula (6) may derive a benzoxazine by fusing two oxazine rings with the active benzene rings of the compound of formula (6). The derived benzoxazine is presented as formula (9):

The exemplary preparation process of the compound of formula (9), derived from the compound of formula (6), is stated in the following description:

To prepare a 5 M solution A', 3.246 g (0.04 mole) of formaldehyde was dissolved in 1.2 ml of dioxane. A 10 M solution B' was prepared by dissolving 1.55 g (0.02 mole) of methylamine in 3 ml dioxane. Solution A' was loaded in a 100 ml reactor and nitrogen was introduced into the reactor in an ice bath. Solution B' was dripped into the reactor at a rate of 1 drop per second under 10° C. The reaction was further progressed for 30 min after the solution B had dropped out. 4.904 g (0.01 mole) of the phosphorus-containing bisphenolic compound of formula (6) was loaded into the reactor and the working temperature was increased until reflux. Then the reaction was further progressed for 10 hours and the solvents were removed by vacuum filtration. The product was dissolved in $CH_2Cl_2$ solution and extracted by 0.1 M NaOH extraction. The extract was washed by deionized water for several times. After the water contained in the reaction system was removed with magnesium sulfate anhydrous, the product was filtrated and dried in a vacuum oven to obtain a pale yellow solid with 80% yield.

According to the embodiments of the disclosure, except the acid catalysts used in above exemplary preparation examples, other catalysts such as a proton acid or a Lewis acid are applicable. The proton acid comprises acetic acid, methanesulfonic acid, calmagite, sulfuric acid, orthanilic acid, 3-pyridinesulfonic acid, sulfanilic acid, hydrogen chloride, hydrogen bromide, hydrogen iodine, hydrogen fluoride, trifluoro acetic acid, nitric acid, or phosphoric acid. The Lewis acid comprises $AlCl_3$, $BF_3$, $FeBr_3$, $FeCl_3$, $BCl_3$, or $TiCl_4$. According to the embodiments of the disclosure, the amount of the acid catalyst used is from 0.1 wt % to 30 wt %.

It will be apparent to those skilled in the art that various modifications and variations can be made to the structure of the disclosure without departing from the scope or spirit of the invention. In view of the foregoing, it is intended that the disclosure cover modifications and variations of this disclosure provided they fall within the scope of the following claims and their equivalents.

What is claimed is:
1. A phosphorus-containing bisphenol defined by a formula (1):

wherein:
$R_1$, $R_2$, $R_3$, and $R_4$ independently are hydrogen atom, halogen atom, an alkyl group having 1-10 carbon atoms, an oxyalkyl group having 1-10 carbon atoms, a haloalkyl group having 1-10 carbon atoms, a cyclic alkyl group having 3-10 carbon atoms, —$CF_3$, or —$OCF_3$;
$R_5$ is an alkyl group having 1-10 carbon atoms or an unsubstituted phenyl group;
A and B are independently selected form the group consisting of —OH, —OCN, and —$Ar^1$ and —$Ar^2$ of formula (1) are independently selected from the group consisting of following groups:

wherein:
$R_6$ is hydrogen atom, a halogen atom, an alkyl group having 1-10 carbon atoms, an oxyalkyl group having 1-10 carbon atoms), a haloalkyl group having 1-10 carbon atoms, a cyclic alkyl group having 3-10 carbon atoms, —$CF_3$, or —$OCF_3$, m is an integer from 0 to 4;
$R_7$ is —OH, —$NH_2$, —$NO_2$, —SH, —COOH, —$SO_3H$, —COH, —$NHCOCH_3$ and —$OCH_3$; and
$R_9$ is nil or —$(CH_2)_p$, and p is an integer from 1 to 20.
2. A phosphorus-containing bisphenol of claim 1, wherein:
$R_1$, $R_2$, $R_3$, and $R_4$ independently are hydrogen atom;
$R_5$ is methyl group;
—$Ar^1$ and —$Ar^2$ independently are phenyl group; and
-A and —B independently are hydroxyl group.
3. A phosphorus-containing bisphenol of claim 1, wherein:
$R_1$, $R_2$, $R_3$, and $R_4$ independently are hydrogen atom;
$R_5$ is phenyl group;
—$Ar^1$ and —$Ar^2$ independently are phenyl group; and
-A and —B independently are hydroxyl group.
4. A method for producing the phosphorus-containing bisphenol according to the claim 1, comprising:

reacting compounds respectively defined by a formula (a), (b), (c) with an acid catalyst; and (a)

(b)

(c)

yielding a phosphorus-containing compound according to claim 1.

5. The method of claim 4, comprising:
reacting compounds respectively defined by a formula (a), (b), (c) with an acid catalyst, wherein $R_1$, $R_2$, $R_3$, and $R_4$ of the compound of formula (a) are independently hydrogen atom; —$Ar^1$, -A, and $R_5$ of the compound of formula (b) respectively are phenyl group, hydroxyl group and methyl group; $Ar^2$ and B of the compound of formula (c) respectively are phenyl group; and
yielding a phosphorus-containing bisphenol has a structure is presented as the follows:

(2)

6. The process of claim 4, wherein the acid catalyst comprises a proton acid or a Lewis acid.

7. The method of claim 6, wherein the proton acid comprises p-toluenesulfonic acid, acetic acid, methanesulfonic acid, calmagite, sulfuric acid, orthanilic acid, 3-pyridinesulfonic acid, sulfanilic acid, hydrogen chloride, hydrogen bromide, hydrogen iodine, hydrogen fluoride, trifluoro acetic acid, nitric acid, or phosphoric acid.

8. The method of claim 6, wherein the Lewis acid comprises $AlCl_3$, $BF_3$, $FeBr_3$, $FeCl_3$, $BCl_3$, or $TiCl_4$.

9. The method of claim 4, wherein the amount of the acid catalyst used is from 0.1 wt % to 30 wt %.

10. The method of claim 4, comprising:
reacting compounds respectively defined by a formula (a), (b), (c) with an acid catalyst, wherein $R_1$, $R_2$, $R_3$, and $R_4$ of the compound of formula (a) are independently hydrogen atom; —$Ar^1$, -A, and $R_5$ of the compound of formula (b) respectively are phenyl group, hydroxyl group and phenyl group; $Ar^2$ and B of the compound of formula (c) respectively are phenyl group; and
yielding a phosphorus-containing bisphenol has a structure is presented as follow:

(6)

11. The method of claim 10, wherein the acid catalyst comprises a proton acid or a Lewis acid.

12. The method of claim 11, wherein the proton acid comprises p-toluenesulfonic acid, acetic acid, methanesulfonic acid, calmagite, sulfuric acid, orthanilic acid, 3-pyridinesulfonic acid, sulfanilic acid, hydrogen chloride, hydrogen bromide, hydrogen iodine, hydrogen fluoride, trifluoro acetic acid, nitric acid, or phosphoric acid.

13. The method of claim 11, wherein the Lewis acid comprises $AlCl_3$, $BF_3$, $FeBr_3$, $FeCl_3$, $BCl_3$, or $TiCl_4$.

14. The method of claim 10, wherein the amount of the acid catalyst used is from 0.1 wt % to 30 wt %.

15. A phosphorus-containing bisphenol defined by a formula (1):

(1)

wherein:

$R_1$, $R_2$, $R_3$, and $R_4$ independently are hydrogen atom, halogen atom, an alkyl group having 1-10 carbon atoms, an oxyalkyl group having 1-10 carbon atoms, a haloalkyl group having 1-10 carbon atoms, a cyclic alkyl group having 3-10 carbon atoms, —$CF_3$, or —$OCF_3$;

$R_5$ is an alkyl group having 1-10 carbon atoms or an unsubstituted phenyl group;

A and B are independently selected form the group consisting of —OH, —OCN, and

—Ar¹ and —Ar² of formula (1) are independently selected from the group consisting of following groups:

* * * * *